(12) United States Patent
Anderson et al.

(10) Patent No.: US 11,130,003 B2
(45) Date of Patent: Sep. 28, 2021

(54) SYSTEMS AND METHODS FOR LASER-ASSISTED TOPICAL TREATMENT OF NAIL FUNGAL INFECTIONS

(71) Applicant: THE GENERAL HOSPITAL CORPORATION, Boston, MA (US)

(72) Inventors: Richard Rox Anderson, Boston, MA (US); Lilit Garibyan, Brookline, MA (US); Kachiu Lee, Wynnewood, PA (US); Oge Onwudiwe, Silver Spring, MD (US); William A. Farinelli, Danvers, MA (US); Dieter Manstein, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/787,270

(22) Filed: Feb. 11, 2020

(65) Prior Publication Data
US 2020/0289844 A1    Sep. 17, 2020

Related U.S. Application Data

(63) Continuation of application No. PCT/US2020/015200, filed on Jan. 27, 2020.
(Continued)

(51) Int. Cl.
*A61N 5/067* (2006.01)
*A61N 5/06* (2006.01)

(52) U.S. Cl.
CPC ...... *A61N 5/0624* (2013.01); *A61N 2005/067* (2013.01); *A61N 2005/0659* (2013.01); *A61N 2005/0661* (2013.01)

(58) Field of Classification Search
CPC ...... A61N 5/06; A61N 5/0613; A61N 5/0616; A61N 5/062; A61N 5/0624;
(Continued)

(56) References Cited

U.S. PATENT DOCUMENTS

| 4,180,058 A | * | 12/1979 | Brem ...... A61B 17/54 128/898 |
| 5,947,956 A | * | 9/1999 | Karell ...... A61B 18/203 606/13 |

(Continued)

FOREIGN PATENT DOCUMENTS

WO    2008109424 A1    9/2008

OTHER PUBLICATIONS

Bhatta, AK, et al, "Fractional carbondioxide (CO2) laser-assisted topical therapy for the treatment of onychornycosis," J Am Acad Dermatol, vol. 74, No. 5, 2016.
(Continued)

*Primary Examiner* — Ahmed M Farah
(74) *Attorney, Agent, or Firm* — Quarles & Brady LLP

(57) ABSTRACT

Systems and methods for a laser-assisted topical treatment of nail fungal infections are provided. The laser-assisted topical treatment includes a laser that is configured to output a beam that penetrates the infected nail and creates a channel therethrough. The laser-assisted topical treatment further includes a treatment agent comprising a vehicle and a drug. The treatment agent is applied to an exterior surface of the infected nail so that the treatment agent may flow into the channel.

15 Claims, 16 Drawing Sheets

Related U.S. Application Data

(60) Provisional application No. 62/848,213, filed on May 15, 2019, provisional application No. 62/818,987, filed on Mar. 15, 2019.

(58) Field of Classification Search
CPC .... A61N 2005/0635; A61N 2005/0642; A61N 2005/0643; A61N 2005/0644; A61N 2005/0659; A61N 2005/0661; A61N 2005/0662; A61N 2005/0667
USPC ................ 607/88–91, 94, 96, 100, 108, 111; 128/898
See application file for complete search history.

(56) References Cited

U.S. PATENT DOCUMENTS

| | | | | |
|---|---|---|---|---|
| 8,523,926 | B2 * | 9/2013 | Neev ............... | C12N 13/00 607/89 |
| 2003/0181847 | A1 * | 9/2003 | Bruno-Raimondi ... | A61K 41/00 604/20 |
| 2006/0212098 | A1 * | 9/2006 | Demetriou ............ | A61B 18/14 607/86 |
| 2007/0144540 | A1 * | 6/2007 | Henrich .................. | A61P 17/06 128/898 |
| 2008/0172047 | A1 * | 7/2008 | Altshuler ............... | A61B 5/441 606/9 |
| 2009/0053290 | A1 | 2/2009 | Sand | |
| 2009/0069741 | A1 * | 3/2009 | Altshuler ............... | A61B 5/441 604/22 |
| 2011/0238003 | A1 | 9/2011 | Bruno-Raimondi | |
| 2020/0237795 | A1 * | 7/2020 | Ray, II ................... | A61K 31/65 |

OTHER PUBLICATIONS

Dai T, et al. Ultraviolet C inactivation of dermatophytes: implications for treatment of onychomycosis. Br J Dermatol. 2008;158(6):1239-46.
De Araujo, R.E. et al. (Jan. 1, 2010) Optical Spectroscopy on Fungal Diagnosis, New Developments in Biomedical Engineering, Domenico Campolo, IntechOpen.
Drugs.com. List of Topical Antifungals + Uses, Types & Side Effects. Located online at https://www.drugs.com/drug-class/topical-antifungals.html. Version as of Oct. 27, 2017.
Erlendsson A, et. al. Fractional Laser-Assisted Drug Delivery: Active Filling of Laser Channels With Pressure and Vacuum Alteration. Lasers in Surgery and Medicine 2016;48:116-124.
Fukshansky L. Revisiting the hexagonal lattice: on optimal lattice circle packing, Elem. Math. 66 (2011) 1-9.
Gupta, A. K., etn al., Fungicidal activities of commonly used disinfectants and antifungal pharmaceutical spray preparations against clinical strains of Aspergillus and Candida species, Medical Mycology 2002, 40, 201-208.
International Searching Authority, International Search Report and Written Opinion for application PCT/US2020/015200, dated Mar. 24, 2020.
Kushwaha, A. et al, Emerging therapies for the treatment of ungual onychomycosis, Drug Dev Ind Pharm, 2015; 41(10): 1575-1581.
Neev J, et. al. Ablation of Human Nail by Pulsed Lasers. Lasers in Surgery and Medicine 21:186-192 (1997).
Nguyen, HX et al., Effect of ablative laser on in vitro transungual delivery, International Journal of Pharmaceutics, 2017.
Okan G, et al. "The Effect of Long-Pulsed Nd:YAG Laser for the Treatment of Onychomycosis," J Am Pod Med Assoc. 2017;107:54-59.
Ozcelik B, 2007. Fungi/Bactericidal and Static Effects of Ultraviolet Light in 254 and 354 nm Wavelengths . Research Journal of Microbiology, 2: 42-49.
Revankar, S. G., Antifungal Drugs, Antifungal Drugs—Infectious Diseases—Merck Manuals Professional Edition, https://www.merckmanuals.com/professional/infectious-diseases/fungi/antifungal-drugs. Accessed online on Feb. 16, 2018.
Saner, M. V., et al., Insights into drug delivery across the nail plate barrier, J Drug Target, 2014; 22(9): 769-789.
Scherer, W. P., et al. Scanning Electron Microscope Imaging of onychomycosis, Journal of the American Podiatric Medical Association, Jul./Aug. 2004, vol. 94, No. 4.
Shivakumar HN, et. al. Ungual and Transungual drug delivery. Drug Development and Industrial Pharmacy.2012; 38(8):901-911.
Su, Xi et al, "Dynamic 3-D shape measurement method: A review," Optics and Lasers in Engineering, 48 (2010) 191-204.
Thorlabs. Laser Scanning Microscopy Tutorial, https://www.thorlabs.com/tutorials.cfm?tabID=8ed9176d-3bbd-4e6c-b2f5-f6a89a2c4fc9. Accessed online on Apr. 8, 2016.
U.S. Food and Drug Administration. "Medical Devices and Clinical Trial Design for the Treatment or Improvement in the Appearance of Fungally-Infected Nails" Guidance Document. Mar. 2016.
Vejnovic I. Systematic investigation of different formulations for drug delivery through the human nail plate in vitro. 2012. In two parts due to file size.
Westerberg D, et. al. Onychomycosis: Current Trends in Diagnosis and Treatment. Am Farn Physician. Dec. 1, 2013;88(11):762-770.

* cited by examiner

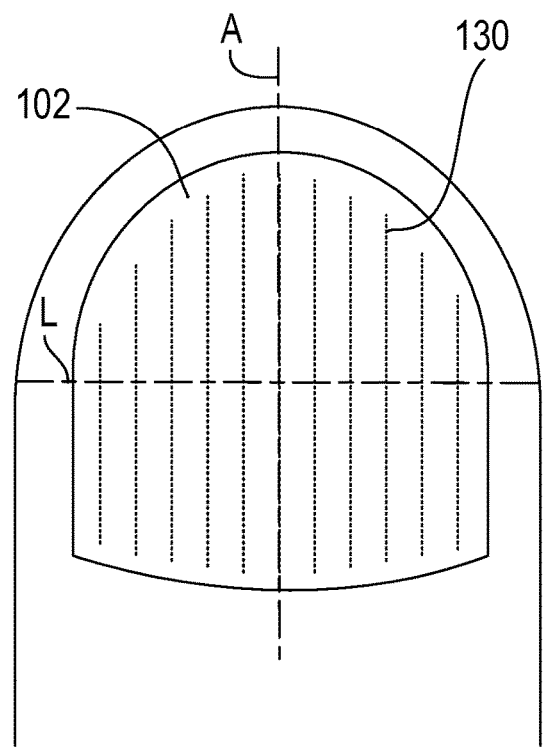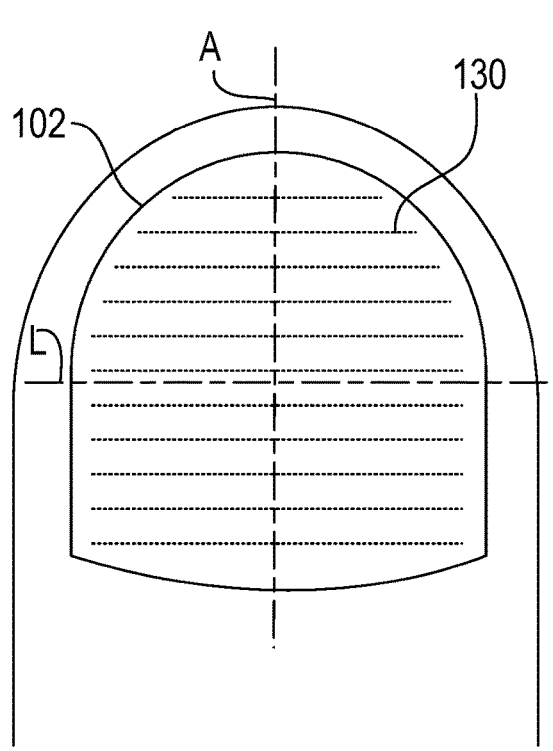
FIG. 9a    FIG. 9b
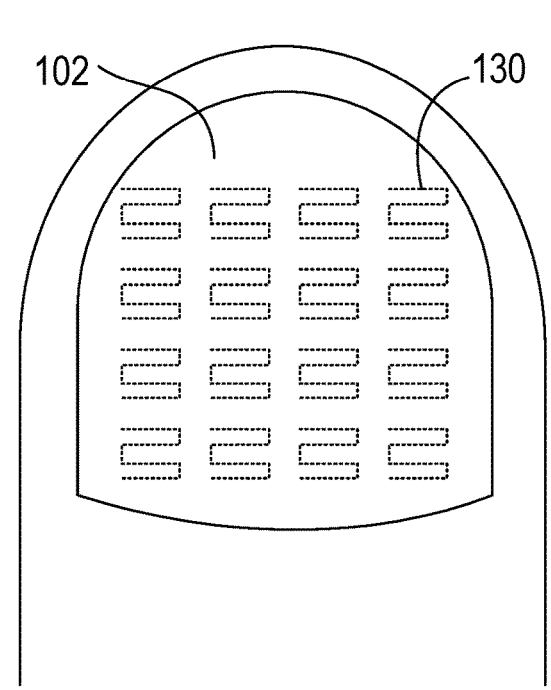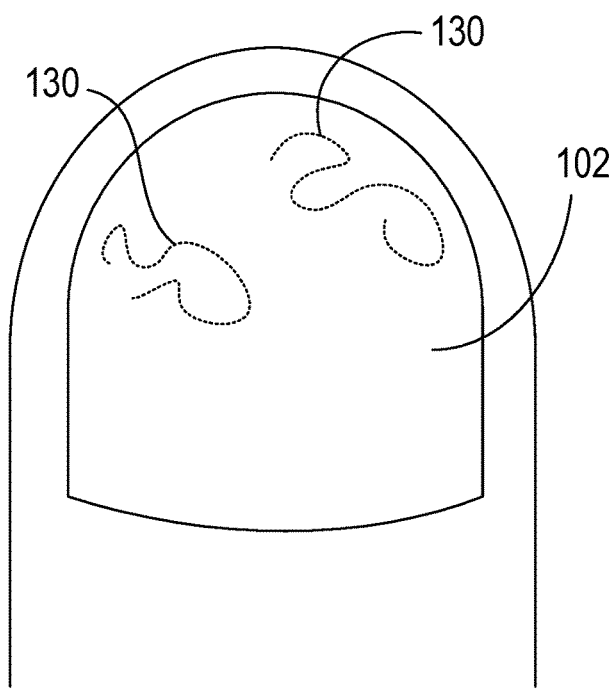
FIG. 9c    FIG. 9d

SYSTEMS AND METHODS FOR LASER-ASSISTED TOPICAL TREATMENT OF NAIL FUNGAL INFECTIONS

CROSS-REFERENCES TO RELATED APPLICATIONS

The present application is a continuation of International Patent Application No. PCT/US2020/015200, which is based on and claims priority to United States Provisional Patent Application No. 62/818,987, filed on Mar. 15, 2019, and United States Provisional Patent Application No. 62/848,213, filed on May 15, 2019, each of which is incorporated herein by reference in its entirety.

STATEMENT REGARDING FEDERALLY SPONSORED RESEARCH

Not Applicable.

BACKGROUND

Onychomycosis is a common nail fungus that typically causes thickened, brittle, crumbly, or ragged nails. Traditionally, treatments of onychomycosis have included topical lacquers, oral antifungal drugs, or nail avulsion.

BRIEF SUMMARY

The present disclosure provides systems and methods for a laser-assisted topical treatment of nail fungal infections.

In one aspect, the present disclosure provides a laser-assisted topical treatment system for treating an infected nail. The treatment system includes a laser and a treatment agent. The treatment agent comprises a vehicle and a drug. The laser is configured to output a beam that penetrates the infected nail and creates a channel therethrough. The treatment agent is applied to a surface of the infected nail and flows into the channel.

In another aspect, the present disclosure provides a method for treating an infected nail using a laser. The method includes positioning the laser relative to the infected nail. Then, a surface of the infected nail is penetrated with the laser to create a channel therethrough. A treatment agent is applied to the surface of the infected nail and flows into the channel.

In another aspect, the present disclosure provides a laser-assisted topical treatment system for treating an infected nail. The treatment includes a laser that moves along a path and output a beam to penetrate through the infected nail and create a plurality of channels therethrough. The treatment further includes a treatment agent that includes a vehicle and a drug. The treatment agent is applied to an exterior surface of the nail and flows into the plurality of channels. The channels are no more than 250 micrometers in width and spaced no more than 1 millimeter apart. Additionally, the treatment agent has a refractive index between 1.45 and 1.55.

BRIEF DESCRIPTION OF DRAWINGS

FIG. 2b is a cross section of the fungal nail of FIG. 2a;

FIG. 3b is a top plan view of the laser-assisted topical treatment system of FIG. 3a;

FIG. 9a is a top plan view of a toe illustrating one path traversed by the laser(s) of a laser-assisted topical treatment system according to the present disclosure;

FIG. 9b is a top plan view of a toe illustrating another path traversed by the laser(s) of a laser-assisted topical treatment system according to the present disclosure;

FIG. 9c is a top plan view of a toe illustrating another path traversed by the laser(s) of a laser-assisted topical treatment system according to the present disclosure;

FIG. 9d is a top plan view of a toe illustrating another path traversed by the laser(s) of a laser-assisted topical treatment system according to the present disclosure;

FIG. 10b is a cross-sectional view of the nail of FIG. 10a;

FIG. 11b is a cross-sectional view of the nail of FIG. 11a;

FIG. 12b is a cross-sectional view of the nail of FIG. 12a;

DETAILED DESCRIPTION

Onychomycosis is a fungal infection of fingernails and toenails. It may cause a nail to become discolored, thickened, and/or brittle. Further, it may cause separation of the nail from its nail bed. Onychomycosis can be difficult to treat and requires a slow treatment process. A common treatment of onychomycosis includes oral antifungal drugs. These oral medications may be effective, but are commonly slow acting and can cause extreme systemic side effects, such as drug interactions, liver failure, arrhythmias, and death. Another common treatment includes topical nail lacquers or nail creams; however, this treatment is usually ineffective and tedious because it requires the nail lacquer or nail cream to be reapplied over a long period of time. Additionally, topical nail lacquers and creams have a limited distance of diffusion into and within nail plates. Consequently, the topical drug may fail to access all infected areas of a fungal nail, such as a subungual space, which is the space beneath a nail. Recently, lasers have been utilized as a method for treating onychomycosis. More specifically, high intensity blue light, as well as photothermal lasers, have been commercialized. Both of these laser treatments require many exposures and are often painful. Therefore, a need exists for a treatment for onychomycosis that is effective, efficient, and minimizes pain.

As will be described, the present disclosure provides systems and methods that can provide treatment for and prevention of fungal nails. More specifically, the present disclosure provides systems and methods that can treat and prevent onychomycosis in an infected nail. The present disclosure provides systems and methods for a treatment that delivers a one-and-done solution for infected nails and can be conducted in an reduced time period (e.g., fifteen minutes), when compared to conventional treatments. More specifically, the laser-assisted topical treatment of the present disclosure may only need to be conducted once or twice in order for it to be effective.

Figure 1:
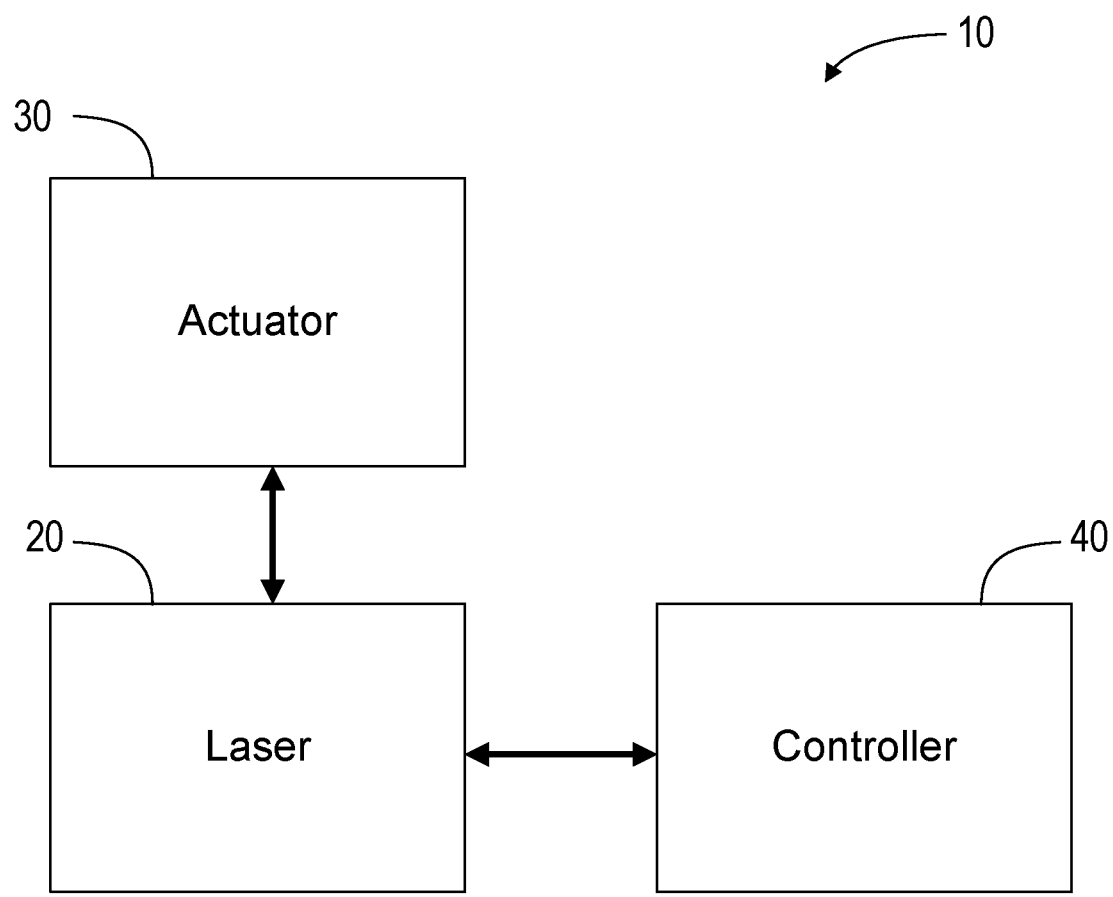
FIG. 1 is a schematic illustration of a laser-assisted topical treatment system according to aspects of the present disclosure.

The systems and methods described herein generally utilize fractional laser ablations to provide a path for a topical drug to penetrate an infected nail. As illustrated in FIG. 1, a laser-assisted topical treatment system 10 for treating onychomycosis according to a non-limiting example of the present disclosure may include a laser 20, an actuator 30, and a controller 40. The controller 40 may be in communication with the laser 20 and the actuator 30, for example, either wirelessly or via a wired connection. In some non-limiting examples, the controller 40 may control activation of the laser 20. For example, the controller 40 may trigger the laser 20 and may determine output parameters of the laser 20 (e.g., pulse width, output power, number of output pulses, output frequency, output energy, a timing of emission, etc.).

In some non-limiting examples, the actuator 30 may be coupled to the laser 20 to move the laser 20 along a path to create a plurality of small channels (e.g., fractional laser ablations) through an infected nail. In some non-limiting examples, the actuator 30 may be configured to move the laser 20 along three-axes of motion relative to an infected nail. In some non-limiting examples, the actuator 30 may be configured to move the laser 20 along one or two axes of motion relative to an infected nail. In some non-limiting examples, the actuator 30 may move the laser 20 along a generally planar path over an infected nail. In some non-limiting examples, the actuator 30 may move the laser 20 along a generally curved path and maintains the laser 20 normal to an exterior (e.g., top) surface of an infected nail. The actuator 30 may be in the form on a pneumatic actuator, an electric actuator, a hydraulic actuator, an electromagnetic actuator, a robotic arm, or another mechanism that may control a position of the laser 20 relative to the infected nail being treated. In general, the controller 40 may activate the actuator 30, which may initiate movement of the laser 20 along a path over the infected nail. In some non-limiting examples, the controller 40 may instruct the actuator 30 to move the laser 20 to a predetermined location (e.g., x, y, z coordinates) over an infected nail.

In some non-limiting examples, the laser 20 may be held stationary and the infected nail being treated may be moved relative to the laser 20.

The laser-assisted topical treatment system 10 further includes a treatment agent (not shown) that includes a vehicle and a drug. Generally, the laser 20 is used to create a plurality of channels through the infected nail, thereby allowing access to a subungual space beneath the infected nail. Then, the treatment agent may be applied to an exterior surface of the infected nail so that the treatment agent may pass through the channels and fill the subungual space. In some non-limiting examples, additional steps may be taken to ensure the treatment agent fills the subungual space, as will be described herein.

Figure 2A:
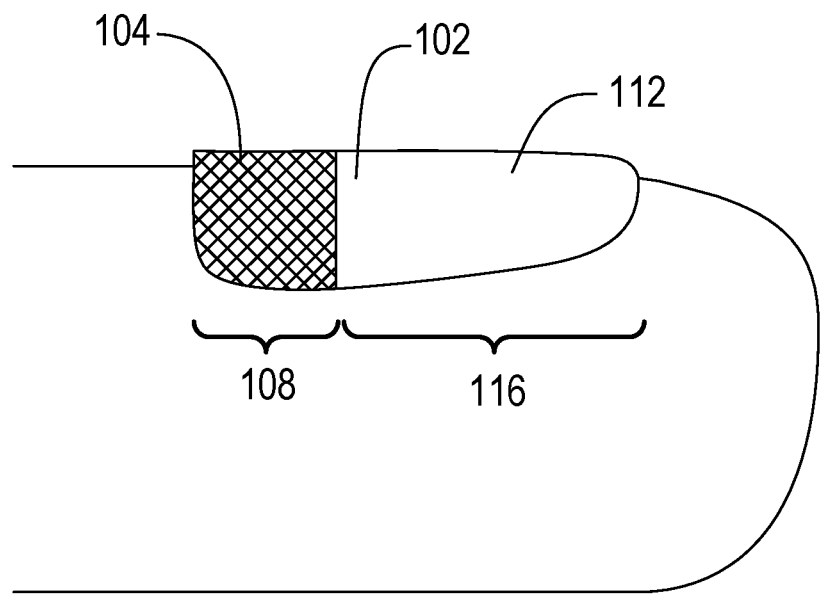
FIG. 2a is a side view of a fungal nail.
Figure 2B:
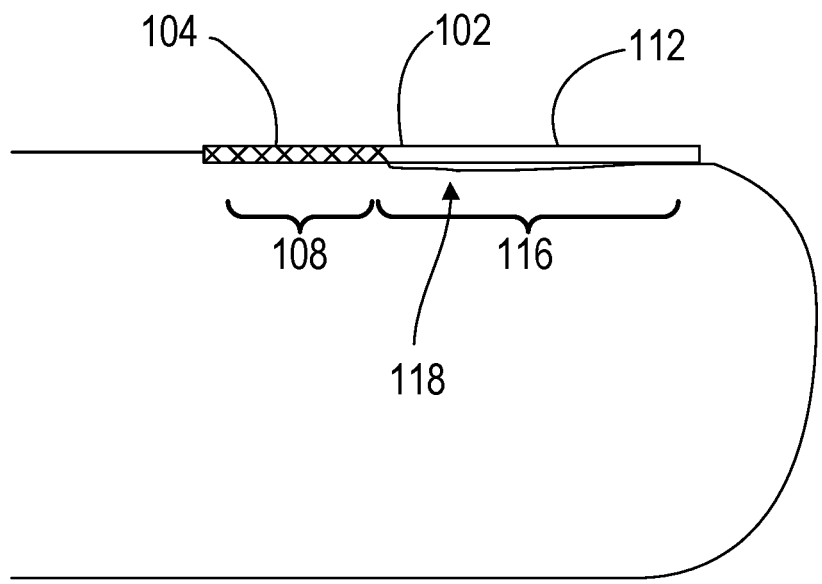

Referring to FIGS. 2a and 2b, the laser-assisted topical treatment system 10 may be intended for a nail 102 that is infected with onychomycosis. The nail 102 may include an uninfected region 104 at a proximal portion 108 of the nail 102 and an infected region 112 at a distal portion 116 of the nail 102. In some instances, the infected region 104 may only occupy 10% of the nail 102. Further, in other instances, the infected region 104 may occupy 50% of the nail or more. In other instances, the infected region 104 may occupy approximately between 50% and 100% of the nail. As described herein, the infected region 104 may experience onycholysis, which is the separation of the nail 102 from skin around it (i.e., a nail bed). If onycholysis occurs, gaps may exist in a subungual space 118 beneath the nail 102. As a result, if the onycholysis occupies a large percentage of the nail 102, the nail could be at risk of avulsion (i.e., tearing or forcibly separating).

Figure 3A:
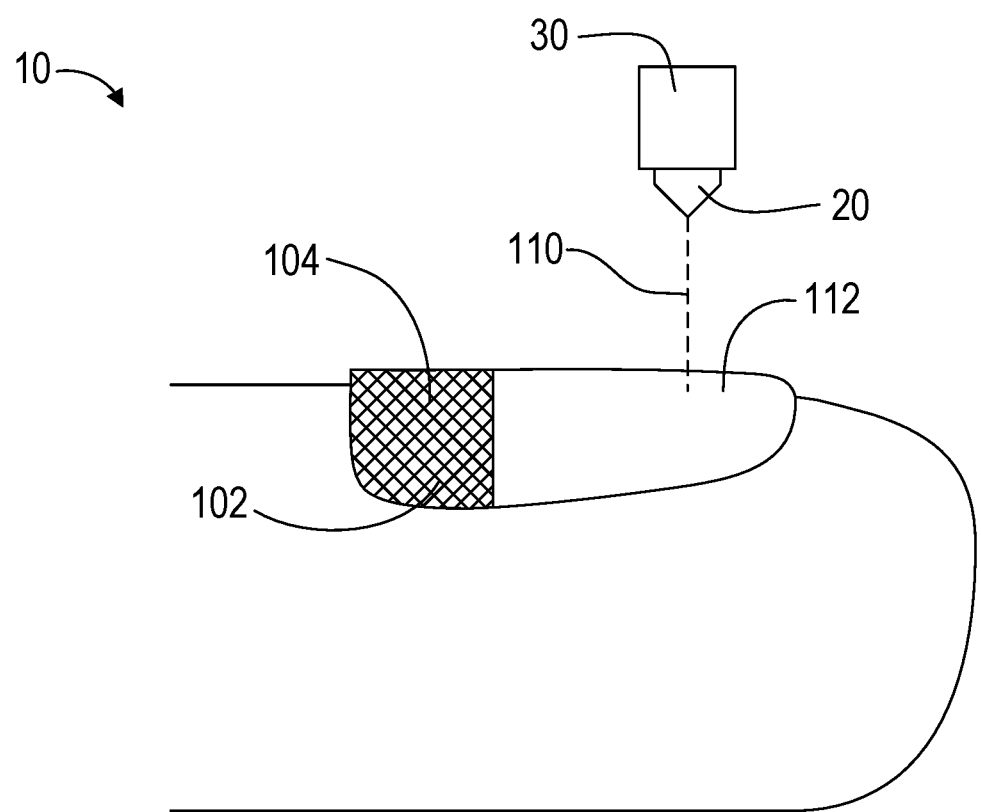
FIG. 3a is a side view of a laser-assisted topical treatment system of FIG. 1 treating a fungal nail.
Figure 3B:
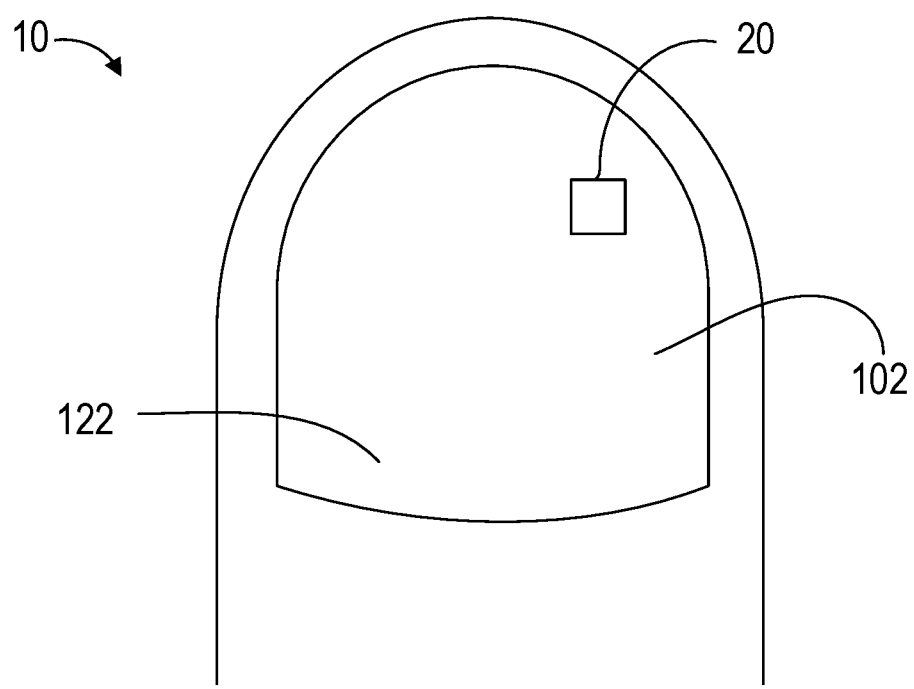

Turning to FIGS. 3a and 3b, the laser 20 of the laser-assisted topical treatment system 10 that may be provided to penetrate the nail 102. In general, the laser 20 may move, for example, via the actuator 30, so that a beam 110 output by the laser 20 may access the entire surface area of a surface 122 the nail 102. In general, the laser 20 may be arranged above the surface 122 of the nail 102 and oriented, such that the beam 110 output by the laser 20 is directed toward the surface 122 of the nail 102. In this way, for example, the beam 110 output by the laser 20 may be used to ablate one or more channels in the surface 122 of the nail 102 that extend through the nail 102.

Figure 4A:
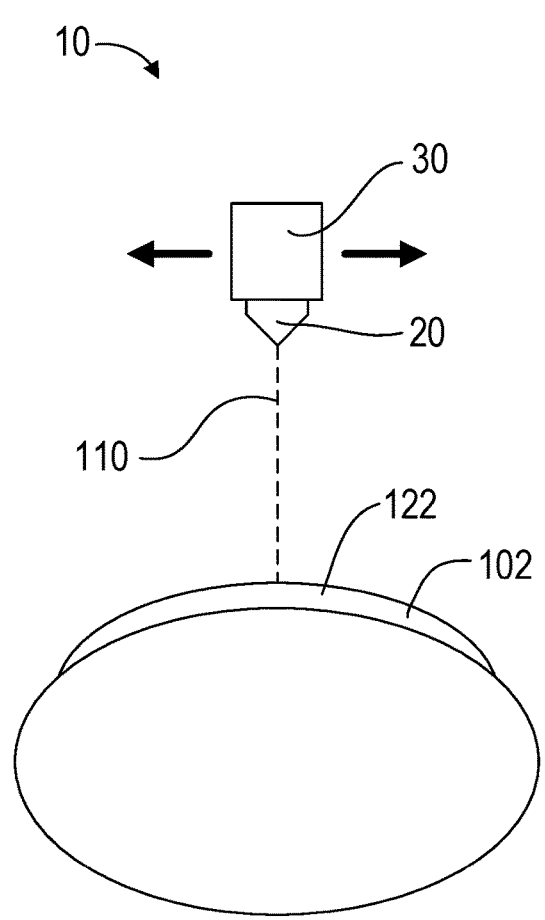
FIG. 4a is a front view the laser-assisted topical treatment system of FIG. 3a with a laser traversing in a planar path.
Figure 4B:
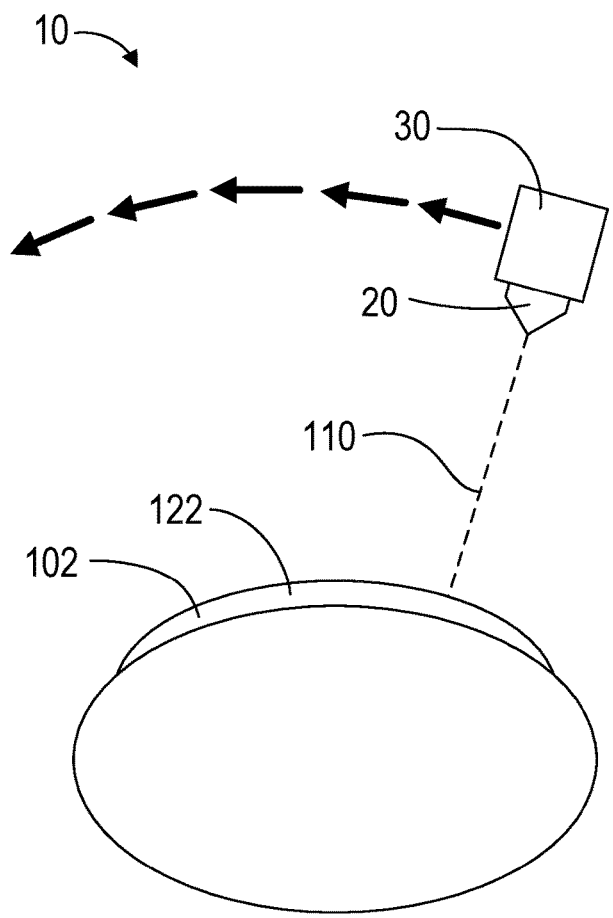
FIG. 4b is a front view the laser-assisted topical treatment system of FIG. 3a with a laser traversing in a curved path.

As described herein, the laser 20 may be movable above the surface 122 of the nail 102. In some non-limiting examples, as illustrated in FIG. 4a, the actuator 30 may move the laser 20 in a planar direction. That is, the laser 20 may be moved in a plane that is arranged generally parallel to a center point on the surface 122 of the nail 102. Alternatively, as illustrated in FIG. 4b, the actuator 30 may move the laser 20 in a generally curved path as the laser 20 moves laterally over the nail 102. In this way, for example, the laser 20 provided may be configured to accommodate the curved surface 122. More specifically, the laser 20 may move relative to the surface 122 of the nail 102 to remain at a consistent distance from the surface 122 throughout a duration of treatment. In other words, the beam 110 output by the laser 20 may remain normal to the surface 122 of the nail 102 as the laser 20 moves laterally across the nail 102.

Figure 5:
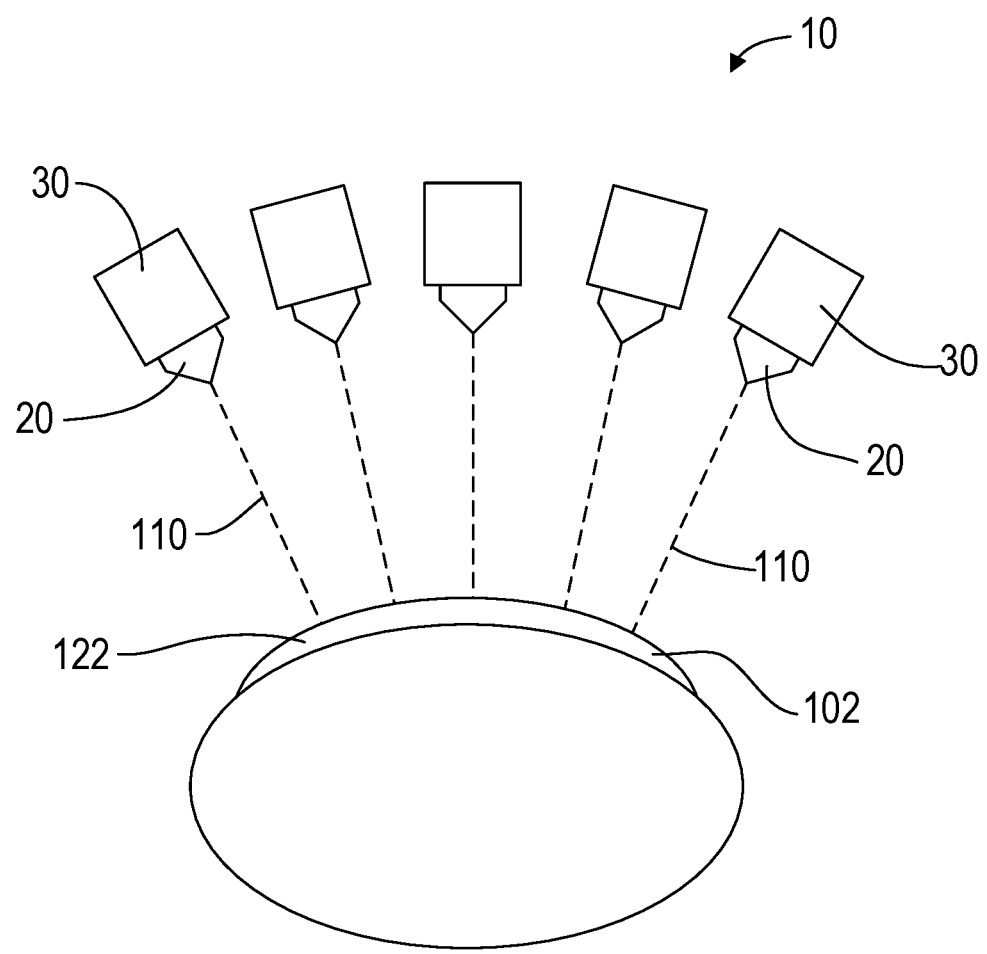
FIG. 5 is a front view a laser-assisted topical treatment system that includes a plurality of lasers.

In the illustrated non-limiting examples of FIGS. 3a-4b, the laser-assisted topical treatment system 10 may include one laser 20. In some non-limiting examples, as illustrated in FIGS. 5-6c, the laser-assisted treatment system may include more than one laser 20. For example, referring to FIG. 5, the laser-assisted treatment system may include a plurality of lasers 20 arrange over the infected nail 102. In the illustrated non-limiting example, the plurality of lasers 20 are laterally spaced over the nail 102 and arranged in a generally curved pattern. That is, each of the lasers 20 may be angled to arrange a beam 110 output thereby is arranged normal to the surface 122 of the nail 102.

Figure 6A:
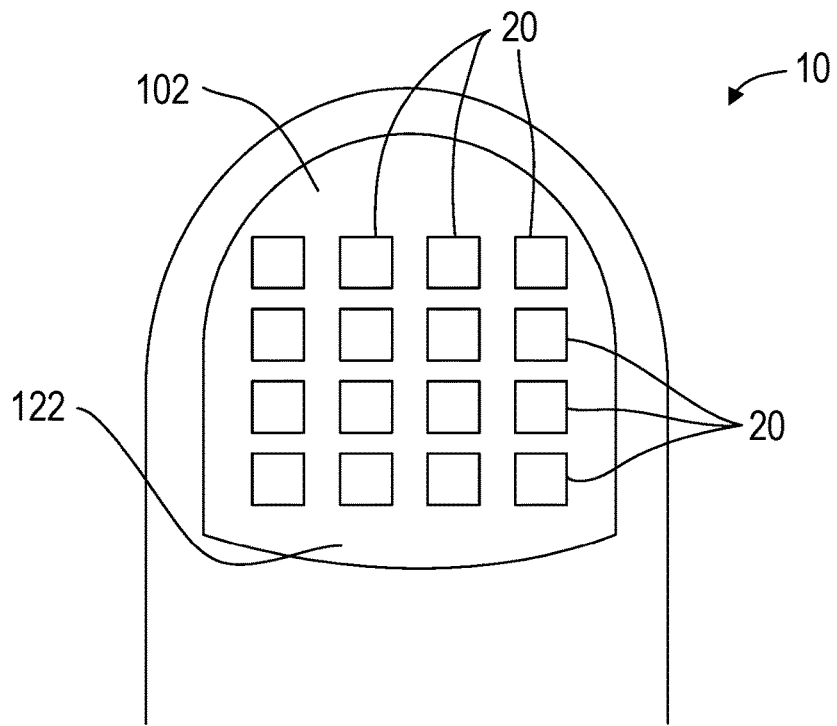
FIG. 6a is a top plan view of the laser-assisted topical treatment system of FIG. 5 with the lasers in a grid pattern.
Figure 6B:
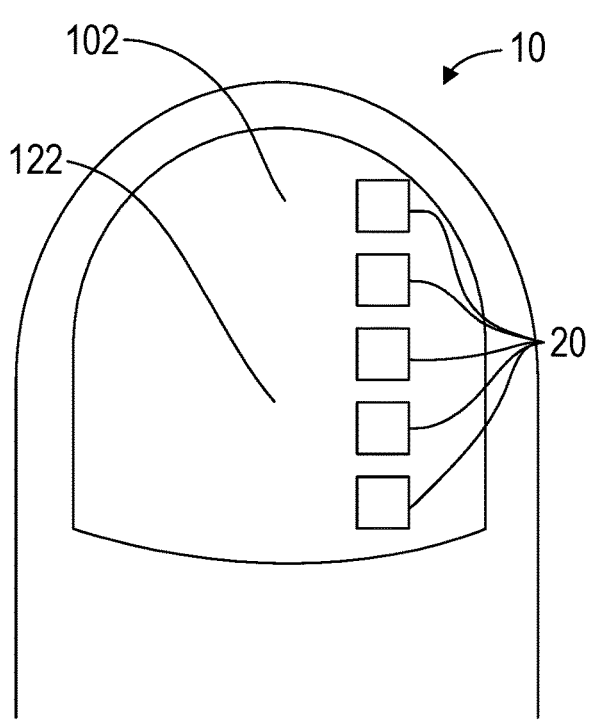
FIG. 6b is a top plan view of the laser-assisted topical treatment system of FIG. 5 with the lasers in a line pattern.
Figure 6C:
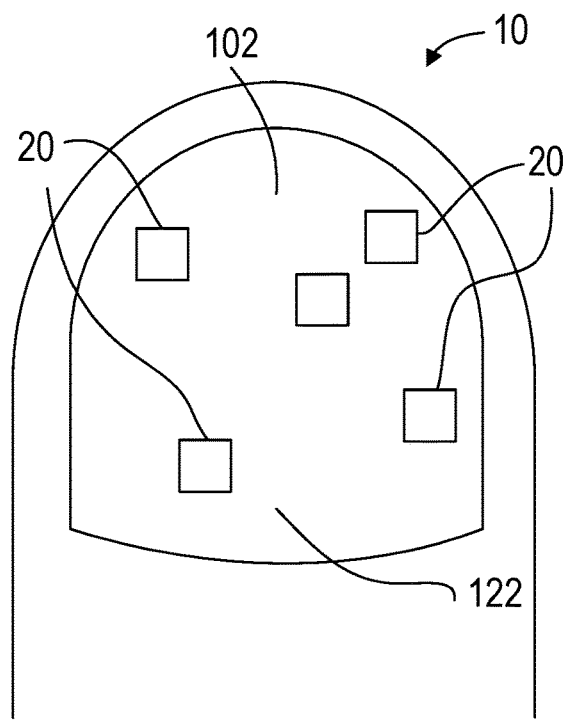
FIG. 6c is a top plan view of the laser-assisted topical treatment system of FIG. 5 with the lasers in a random pattern.

Turning to FIGS. 6a-6c, the lasers 20 may be organized over the nail 102 in various arrangements. For example, referring to FIG. 6a, the plurality of lasers 20 may cover a substantial portion of the infected nail 102. That is, the plurality of lasers 20 may be arranged in a grid formation with the lasers 20 arranged in generally parallel rows and columns. Additionally or alternatively, as shown in FIG. 6b, the lasers 20 may be oriented in a single row. Although the illustrated example of FIG. 6b shows the lasers 20 being arranged in a row that extends from a distal end of the nail 102 to the proximal end of the nail 102, the lasers 20 may be arranged in a row that extends laterally across the nail 102. Furthermore, referring to FIG. 6c, the lasers 20 may be positioned in a random pattern. Utilizing more than one laser 20 may increase efficiency of the laser-assisted topical treatment according to the present disclosure. For example, a duration of the treatment may be deceased, since a larger surface area of the nail 102 may be treated simultaneously.

Figure 7A:
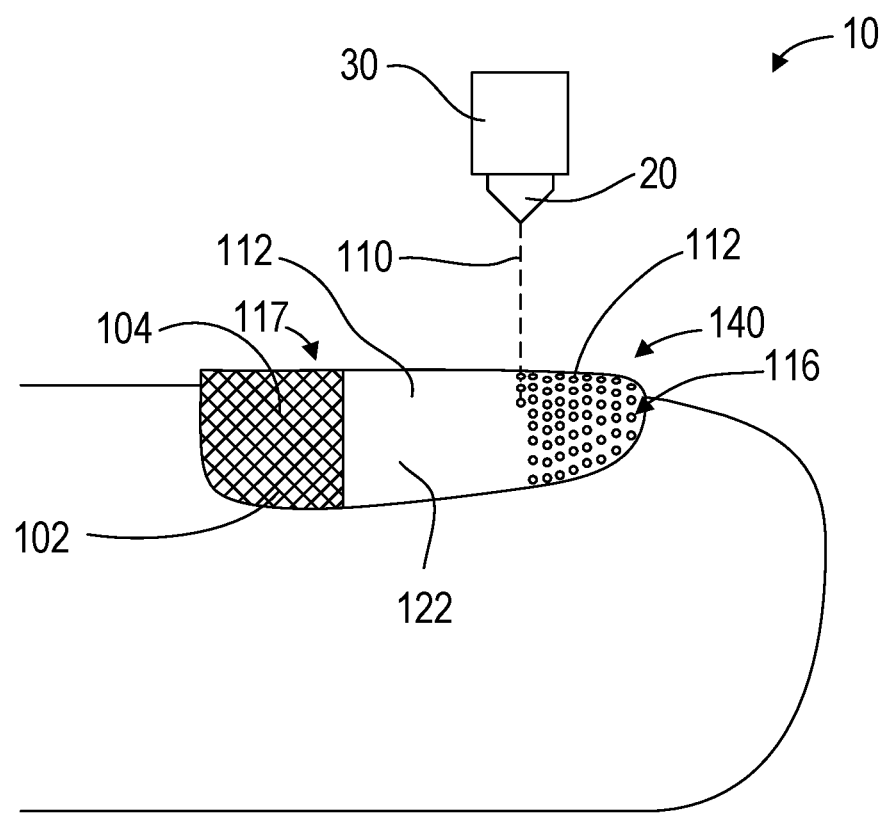
FIG. 7a is a side view of the laser-assisted topical treatment system of FIG. 3a during treatment of a distal portion of a nail.

Referring to FIG. 7a, during operation, the laser 20 may be trigger by the controller 40 to output one or more beams 110 that are directed at various location on the surface 122 of the nail 102. The beams 110 incident on the surface 122 of the nail 102 may remove material from the nail 102 to form a channel 140 that extends through the nail 102. In some non-limiting example, a sequence of beams 110 may be output by the laser 20 in the same location on the surface 122 of the nail 102 until the channel 140 extends through the nail 102. As the laser(s) 20 are moved along a predetermined path, the laser 20 may continue to output one or more beams 110 in a given location to create a plurality of channels 140 through the nail 102.

Figure 7B:
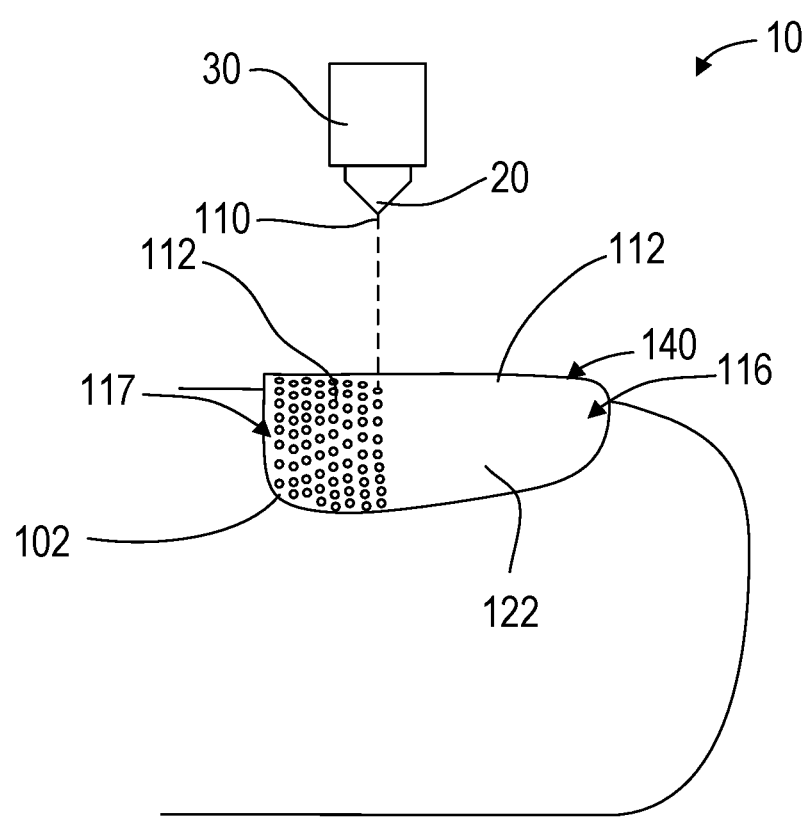
FIG. 7b is a side view of the laser-assisted topical treatment system of FIG. 3a during treatment of a proximal portion of a nail.
Figure 8A:
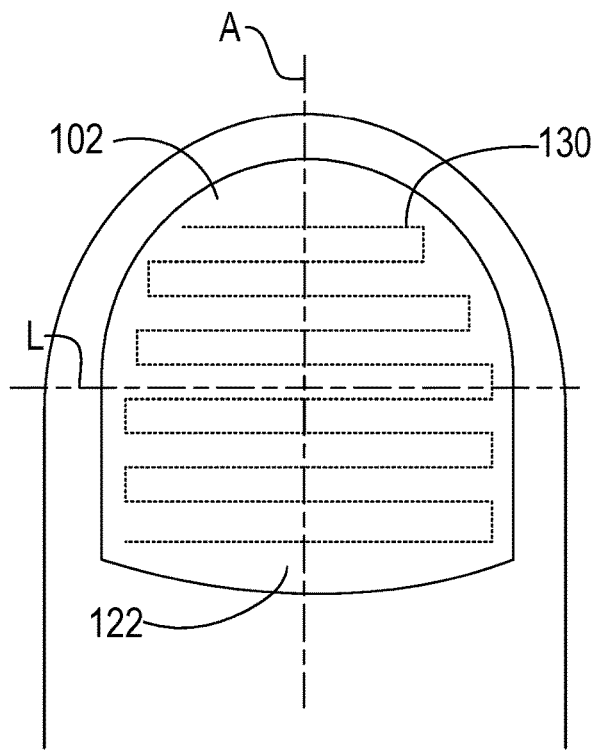
FIG. 8a is a top plan view of a toe illustrating a path traversed by the laser(s) of a laser-assisted topical treatment system according to the present disclosure.
Figure 8B:
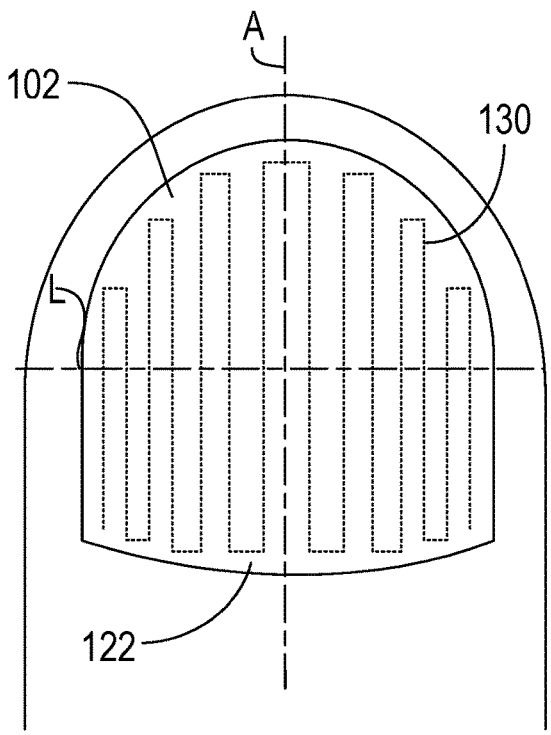
FIG. 8b is a top plan view of a toe illustrating another path traversed by the laser(s) of a laser-assisted topical treatment system according to the present disclosure.
Figure 8C:
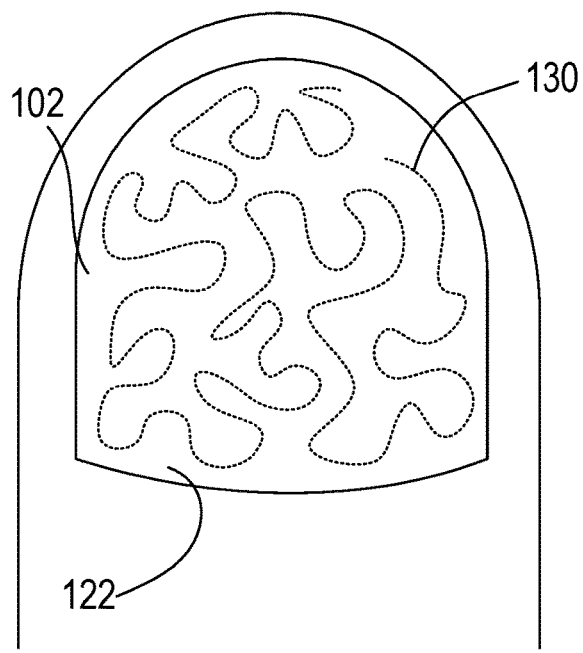
FIG. 8c is a top plan view of a toe illustrating another path traversed by the laser(s) of a laser-assisted topical treatment system according to the present disclosure.
Figure 8D:
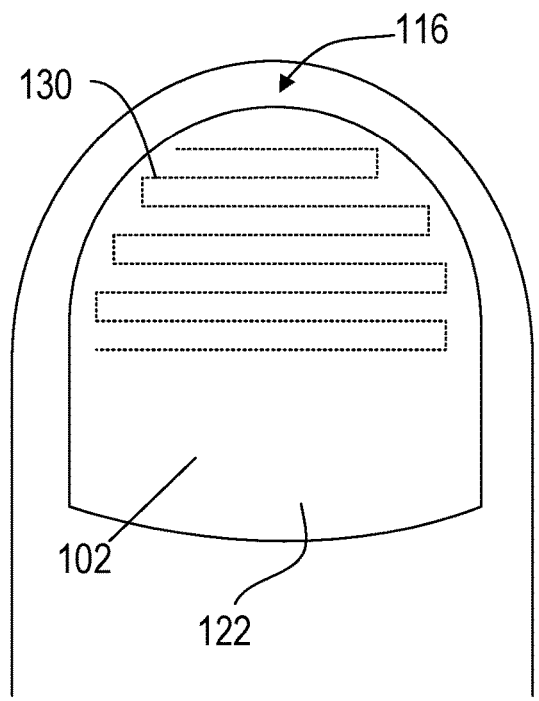
FIG. 8d is a top plan view of a toe illustrating another path traversed by the laser(s) of a laser-assisted topical treatment system according to the present disclosure.

FIGS. 8a-8d depict non-limiting examples of a path 130 the laser 20 (see, e.g., FIGS. 7a and 7b) may move along. For example, as shown in FIG. 8a, the laser may track in a lateral direction, indicated by axis L, across the infected nail 102 in alternating directions while incrementally moving across the nail 102 in an axial direction, indicated by axis A. Additionally or alternatively, as shown in FIG. 8b, the laser may move along the axial direction A in alternating directions while moving over the nail 102 in the lateral direction L. However, the laser 20 according to the present disclosure may not move along a symmetric path, as illustrated in FIGS. 8a and 8b. For example, an additional non-limiting example is shown in FIG. 8c where the path 130 may be random and/or non-linear. Further, the path 130 may be tailored to an individual undergoing treatment (i.e., customized).

Although FIGS. 8a-8c illustrate a laser moving along a path that covers approximately the entire surface area of the surface 122 of the infected nail 102, the laser 20 may not need to ablate all areas of the nail 102. Rather, it may be desirable for the laser 20 to ablate only a portion of the nail 102. More specifically, in some instances, it may be desirable for the laser 20 to ablate between 40% and 50% of the infected nail. In some instances, it may be desirable for the laser 20 to ablate between 30% and 60% of the infected nail. In some instances, it may be desirable for the laser 20 to ablate between 20% and 70% of the infected nail. In some instances, it may be desirable for the laser 20 to ablate between 10% and 80% of the infected nail. In some instances, it may be desirable for the laser 20 to ablate between 0% and 90% of the infected nail.

For example, as shown in FIG. 7a, onychomycosis often begins at the distal portion 116 of the nail 102, i.e., the fungal infection starts near a tip of the nail 102 and may not infect the entire nail plate. As such, only the distal portion 116 of the nail 102 may require treatment. Alternatively, as shown in FIG. 7b, a proximal portion 117 of the nail 102 may be treated (e.g., ablated to for a plurality of channels therethrough). In this way, for example, the treatment agent applied to the nail 102 may be applied over the nail 102 (e.g., disperse from the proximal portion 117 to the distal portion 116) as the nail 102 naturally grows.

FIGS. 9a-9d provide non-limiting examples of paths the plurality of lasers 20 may move along, according to aspects of the present disclosure. Referring to FIG. 9a, the plurality of lasers 20 may be spaced laterally and may move along a linear path 130, such as along the axial direction A of the nail 102. Additionally or alternatively, referring to FIG. 9b, the plurality of lasers 20 may be spaced axially and may move along a linear path 130, such as along the lateral direction L. If the plurality of lasers 20 are positioned in a grid, for example, similar to the configuration of FIG. 6a, the plurality of lasers 20 may move synchronously along a path 130, as illustrated by FIG. 9c. Further, additionally or alternatively, the plurality of lasers 20 may move independent from each other and/or along a random, non-linear path 130, as shown in FIG. 9d.

In general, the path 130 and the corresponding pattern of the plurality of channels 140 formed in the nail 102 may take any form, including, for example, one of the paths 130 disclosed herein and/or a combination of two or more of the paths 130 disclosed herein. In some non-limiting examples, the plurality of channels 140 may be formed locations that provide access to an injected region of the nail 102. Alternatively of additionally, the plurality of channels 140 may be formed in locations that provide access to the subungual space 118 of the nail 102 (see, e.g., FIGS. 10a and 10b).

Figure 10A:
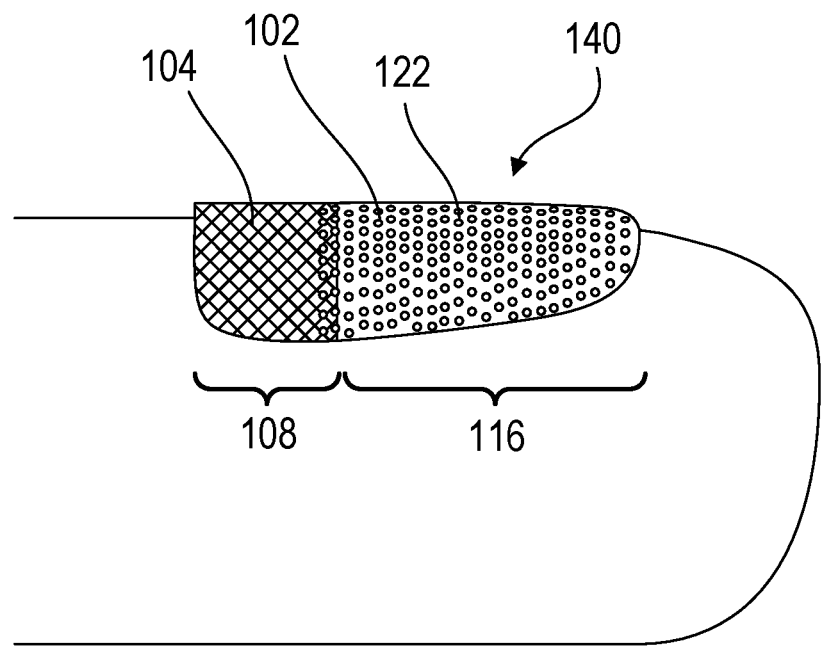
FIG. 10a is a side view of the toe nail of FIG. 7 after laser ablation.
Figure 10B:
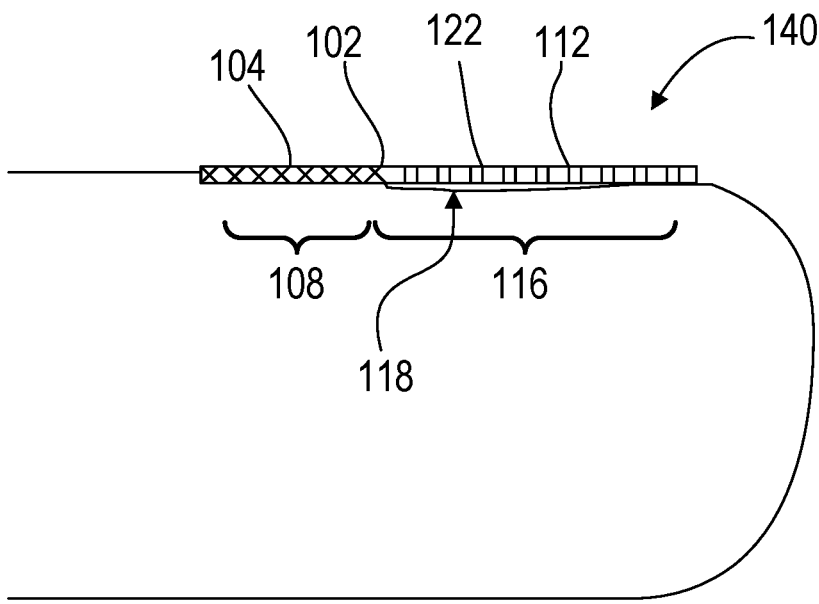

FIGS. 10a and 10b illustrate one non-limiting example of the nail 102 after the laser(s) 20 ablated an infected region 112 of the nail 102, thereby forming a plurality of channels 140 through the nail 102. As best seen in FIG. 10b, each of the plurality of channels 140, or at least a portion of the plurality of channels 140, may completely extend through the nail 102 into the subungual space 118. If complete onycholysis exists, the subungual space 118 may include a continuous gap beneath the nail 102. Further, in some instances, partial onycholysis may occur. That is, onycholysis may be patchy, so the subungual space 118 may include scattered gaps beneath the nail 102. In general, at least one of the plurality of channels 140 may provide access to the subungual space 118 from the surface 122 of the nail 102.

Figure 11A:
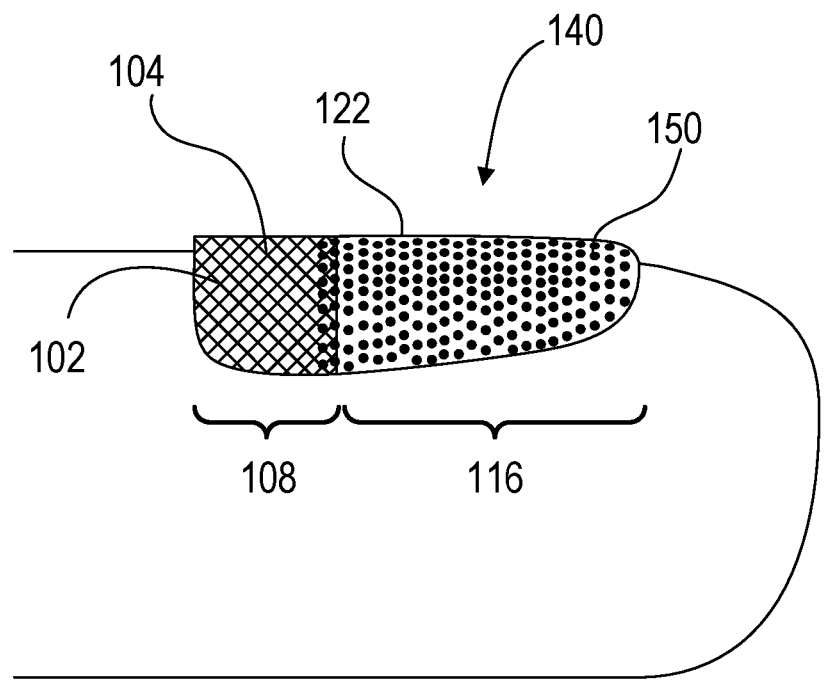
FIG. 11a is a side view of the nail of FIG. 10a after a treatment agent is applied.
Figure 11B:
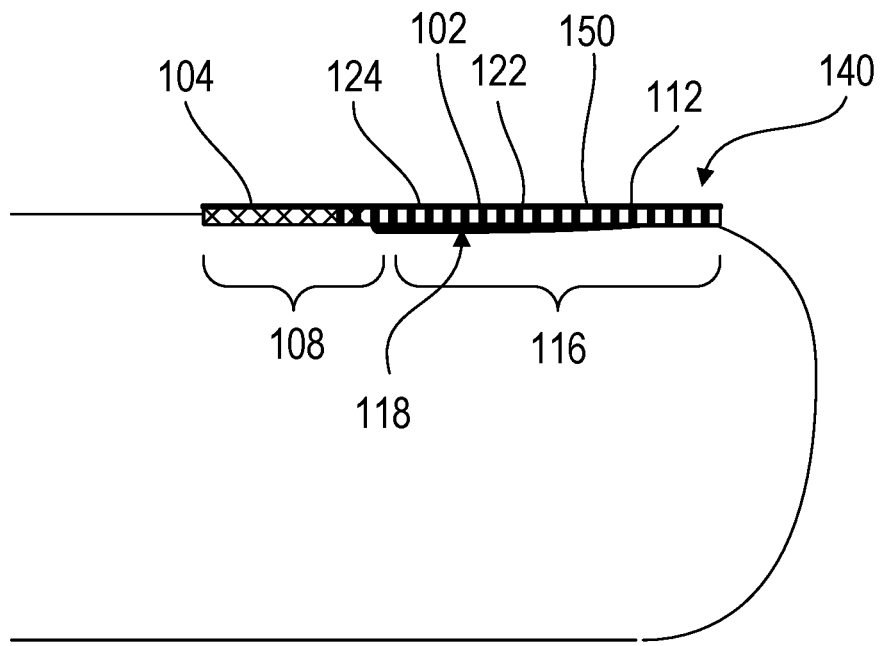

Referring to FIGS. 11a and 11b, once the laser has created the plurality of channels 140, preferably through the infected region 112 and, in some instances, through a portion of an uninfected region 104 adjacent thereto, the nail 102 is ready for a treatment agent 150 to be applied thereto. For example, the treatment agent 150 may comprise at least an active drug. In some non-limiting examples, the treatment agent 150 may comprise at active drug and a vehicle. The treatment agent 150 may be applied to the surface 122 of the nail 102 so that the treatment agent 150 may pass through the plurality of channels 140. With the treatment agent 150 arranged at least partially within the plurality of channels 140, the treatment agent 150 is capable of occupying a larger amount of surface area of the nail 102 when compared to conventional treatment lacquers, which may enhance the effectiveness of the treatment agent 150. Further, because the channels 140 provide access to the subungual space 118, the treatment agent 150 may flow into and engage the subungual space 118. If partial or complete onycholysis has occurred, the treatment agent 150 may fill any existing gaps between the nail 102 and the nail bed.

Figure 12A:
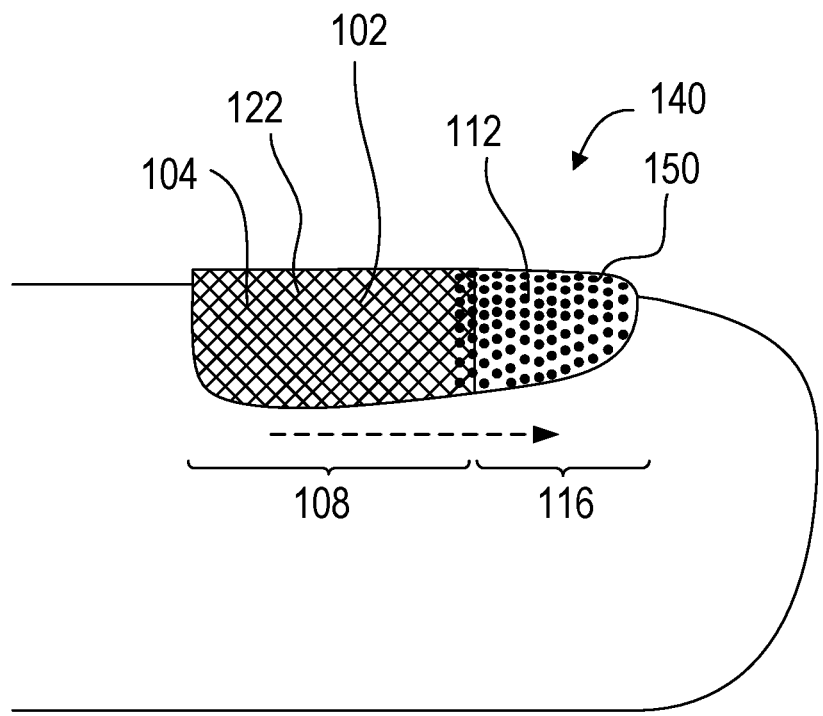
FIG. 12a is a side view of the nail of FIG. 11a after natural growth.
Figure 12B:
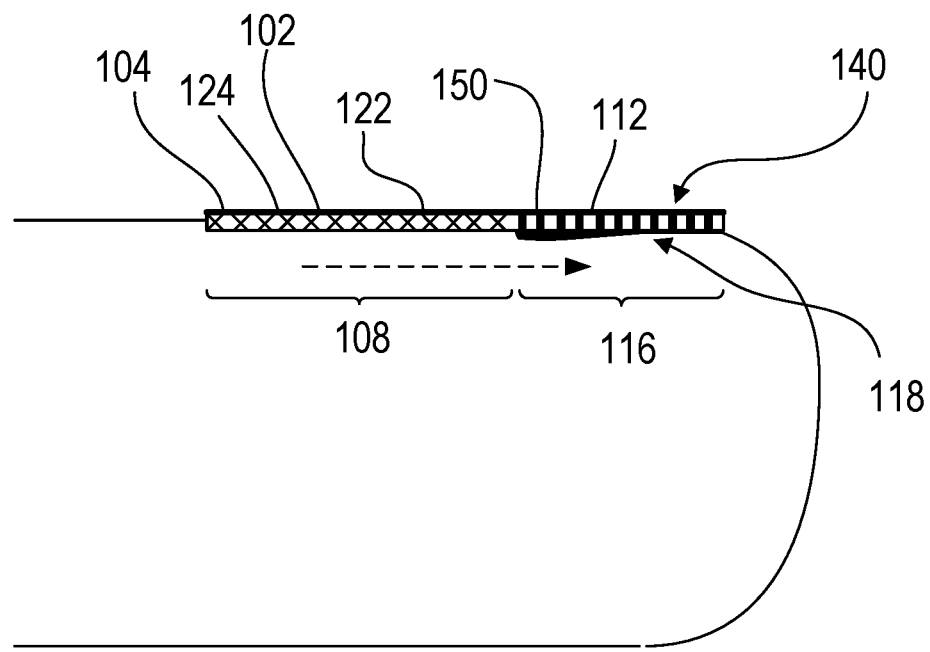
Figure 13:
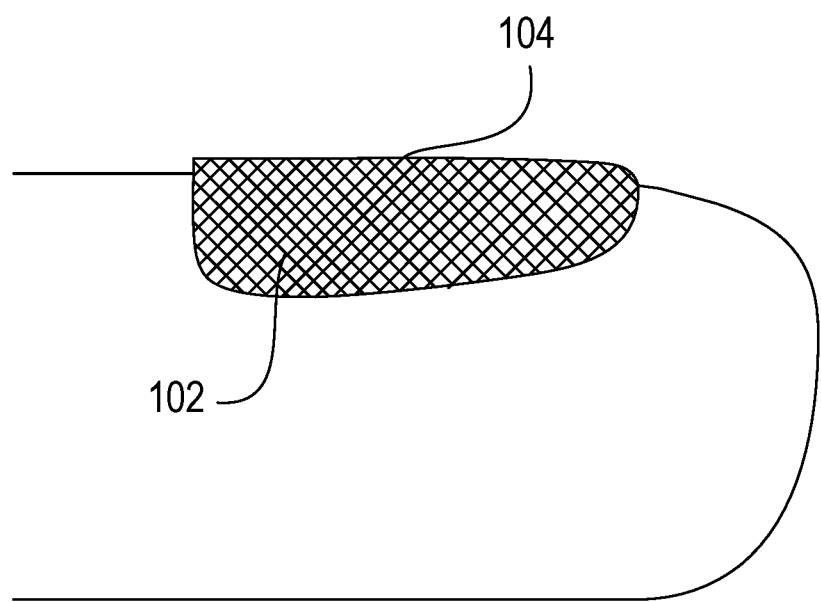
FIG. 13 is a side view of the nail of FIG. 11a after a successful treatment.

Turning to FIGS. 12a-13, as previously stated, the laser-assisted topical treatment system 10 may be implemented to treat an infected nail with onychomycosis. By providing access to the subungual space 118, the treatment agent 150 is capable of accessing a greater portion of the infected nail 102 when compared to conventional treatments. As a result, the drug in the treatment agent 150 may be more effective. Furthermore, an aspect of the present disclosure may be to provide a one-and-done treatment for onychomycosis. That is, the laser-assisted topical treatment may only need to be applied once. As illustrated in the regression of the infected region 112 from FIG. 11a to FIG. 13, the treatment agent 150 may remain within the infected region 112 and/or the subungual space 118 as the nail grows and the uninfected region 104 lengthens. Therefore, the treatment agent 150 may remain intact as the nail 102 grows naturally until the infected region 112 is clipped away, and only the uninfected region 104 exists (FIG. 13).

As discussed above, existing treatments for onychomycosis frequently require multiple applications in order to be effective. Thus, these existing treatments are tedious and commonly ineffective. Therefore, the present disclosure intends to provide a one-and-done solution for onychomycosis that is simple and effective. For example, the laser-assistant topical treatment of the present disclosure may only need to be applied once or twice for it to be effective. In order for the one-and-done treatment to be successful, delivery of the drug must be prolonged. That is, the drug should remain active and adequate at least as long as the infected nail takes to grow naturally and be removed by normal clipping. For example, a great toenail may take as long as six months to grow out. Therefore, the drug may need to remain active for as long as six months in order to successfully treat the great toenail's infection.

However, if the drug concentration depletes over a duration of time (e.g., one month), then that duration of time should approximately define an appropriate interval between treatments. As such, the treatment should be repeated at that interval until the infected nail grows out and is replaced by a healthy nail. Using the previous example, a great toe nail plate is typically replaced by natural growth in approximately six months. Therefore, the drug should remain present and active for that duration of time. Otherwise, additional treatments should be conducted at a defined interval until the nail has grown out. Further, onychomycosis is often distal, meaning that the fungal infection starts near a tip of the nail and may not manage to infect the entire nail plate. As such, the laser-assisted topical treatment according to the present disclosure may only need to be performed over a distal portion of an infected nail. The duration needed for sustained antifungal drug delivery may be somewhat shorter if only the distal portion of the nail is treated. Additionally or alternatively, the laser-assisted topical treatment according to the present disclosure may simply be applied to a proximal portion of the nail to allow fungi to be eliminated in a "push-broom" fashion as the nail grows.

Although a preferred aspect of the present disclosure would be to provide a one-and-done treatment, the one-and-done treatment may not be appropriate for all cases of infected nails. For example, after an original treatment of an infected nail, and as the nail grows, new areas of the infected nail may become infected. Therefore, an additional treatment may be required to successfully treat the infection. If the additional treatment is required, it may be important that the treatment agent used during the original treatment reacts to laser ablation in a manner very similar to that of the infected nail. That is, the treatment agent 150 should not ignite, loose adhesion, carbonize, or obviously discolor upon laser exposure from the laser(s) 20. Ensuring the treatment agent can handle laser exposure would allow for the additional treatment to be applied to the nail without regard for patterns and areas that were originally treated (i.e., the infected nail can be treated like it is a new, untreated nail). Additionally, onychomycosis begins as a skin infection. Therefore, a critical step to prevent infection and/or reinfection of the nail is to treat skin surrounding the nail. Hence, it may be desirable for the laser-assisted topical treatment of the present disclosure to be used in combination with an existing topical treatment, such as an antifungal cream, powder, or spray.

Ideally, the treatment agent 150 may provide sustained presence and concentration of the drug in the nail plate for a duration of time longer than the time needed for replacement of the nail by natural growth. A prolonged delivery and sustained presence of an effective level of the antifungal drug within the infected nail may be accomplished by a combination of a sufficiently high volume fraction, a sufficiently high drug concentration, and a stable drug. The maximum volume fraction of the treatment agent in the nail is equal to the volume fraction of ablation (i.e., removal). For example, if 50% of the nail has been ablated, then up to 50% of the nail volume can be filled with the treatment agent. Additionally or alternatively, the treatment agent may be provided both on the nail's outer surface (e.g., the surface 122) and at the nail bed to increase the volume fraction. More specifically, and preferably, an additional covering layer (see, e.g., covering layer 124 of FIG. 11b) of the treatment agent may be applied to the outer surface of the nail (e.g., the surface 122), such as with existing nail lacquers or creams. The covering layer, for example, may be a nail lacquer that a patient can apply once per week at home. In some instances, the covering layer may form a reservoir for holding the treatment agent and can be refilled. In this instance, a pressure source may be used to supply alternating positive and negative pressure to the nail to promote flow of the treatment agent into the reservoir. Further, in some instances, the covering layer may act as a barrier to ensure the treatment agent remains in channels 140 and/or the subungual space 118. Furthermore, if onycholysis has occurred, the treatment agent 150 may be additionally applied underneath the nail and directly on the nail bed. However, onycholysis may be patchy, which may lead to blind gaps between the nail plate and nail bed; therefore, delivery of the drug via laser ablation may fill these gaps. Furthermore, for infected nails with onycholysis, using a vehicle that enters the subungual space and binds to the overlying nail can greatly reduce reinfection by way of the subungual route. Thus, it is highly desirable for the vehicle and drug to enter the nail through the plurality of channels 140, fill the channels 140 with the treatment agent 150 comprising the vehicle and drug, enter and fill the subungual space, and bind to both the nail plate and nail bed.

A partition coefficient of the drug is another important factor to ensure prolonged release of the drug. A drug partition strongly favoring the vehicle of the treatment agent may lead to a slow release of the drug. Additionally, when the drug partition strongly favoring the vehicle is combined with a high drug concentration and/or timed release of the drug from sites within the vehicle (e.g., crystalline drug particles, encapsulated drugs, stable liposomes, etc.), plus a high volume fraction, the result may be a very prolonged drug release (i.e., a sustained drug presence may be achieved). One non-limiting example of a drug that may be used as a treatment agent ingredient is terbinafine, which is a cidal antifungal agent that is highly insoluble in water and aqueous (polar) media. If the treatment agent further includes a polar polymer as the vehicle into which crystalline particles of terbinafine are embedded, the drug content of the treatment agent may slowly deplete due to low solubility of the drug through the vehicle and low partitioning into the nail. Using a treatment agent 150 similar to the aforementioned example may be desirable for the present disclosure because of the configuration of the plurality of channels 140. That is, in some instances, the plurality of channels 140 may be spaced less than or equal to one millimeter apart. Further, in some instances, the plurality of channels 140 may be spaced fifty to two hundred micrometers apart. Therefore, because the plurality of channels 140 may be closely spaced, the drug may not need to diffuse a long distance. Furthermore because the proximity of the channels 140 may ensure that the drug is not lost to its surrounding, a high drug concentration may persist throughout a duration required for complete nail regrowth.

To achieve a plurality of small channels spaced close to each other, the laser-assisted topical treatment system according to the present disclosure may use a laser 20 with an output beam 110 in the ultraviolet ("UV") range, for example, with output wavelengths less than approximately 400 nanometers (nm). Further, the laser(s) 20 may operate at wavelengths less than 350 nm. UV photons have short wavelengths, which may allow for the laser(s) 20 to focus on small spots. For example, using a UV laser at approximately 240 nm may be desirable for the laser-assisted treatment of the present disclosure because it can produce small channels. Therefore, the channels 140 may have widths of two hundred fifty micrometers or less. Additionally or alternatively, near-infrared lasers with high beam quality may be utilized. Using a laser with a very short pulse, for example, picosecond or femtosecond pulse durations, may be desired in order to achieve a plurality of narrow channels 140. For example, the laser 20 may operate with a pulse duration of 1 nanosecond or less.

Providing the plurality of channels 140 through the nail, as may be required by the present disclosure, may result in a mechanically weak nail due to a large ablated volume fraction and very small separation between the adjacent channels 140. More specifically, the nail plate, which may be already weakened by partial fungal digestion, may become very weak after laser ablation processing. As such, the laser-processed nail may be prone to breakage, erosion, and loss. Further, if onycholysis is also present, the loss may be equivalent to an uncontrolled nail avulsion. Therefore, in order to mitigate such issues, the present disclosure may provide aspects to restore mechanical properties of the infected nail. Restoring mechanical properties of the infected nail can be met by ensuring that the vehicle of the treatment agent 150 is mechanically robust. In order for the vehicle to restore mechanical properties to the nail, a combination of tensile strength, elasticity, and binding strength are important characteristics. Additionally, if the nail has experienced partial or complete onycholysis, it may be desirable for the vehicle to restore attachment of the nail to its nail bed.

As with some cosmetic nail materials, light may be used to activate polymerization and/or hardening of the vehicle, and to control the degree of crosslinking, which in turn may affect both tensile strength and elasticity of the vehicle. As such, the vehicle may incorporate a visible or ultraviolet cured polymer. Alternatively or additionally, as a mechanism to achieve a mechanically robust material, the vehicle may employ a composite structure. For example, glass fiber may be used in an acrylic or epoxy vehicle to create "fiberglass." Using a composite may result in a more mechanically robust vehicle than would result from using individual component materials alones. As additional non-limiting examples, fibrous, particle, or crystalline materials may be combined with polymer, adhesive, or other materials to form a robust composite. Furthermore, the antifungal drug itself may be a solid-phase component of the composite. For example, the antifungal drug may include keratin or collagens, which are structural proteins that may occur as fibers.

Additional desired properties of the treatment agent according to the present disclosure include non-irritating, non-allergenic, stable, and non-toxic. More specifically, because the vehicle is in contact with skin around the infected nail, an additional requirement may be that the vehicle in the treatment agent 150 not be an irritant or allergen. It may also be desired, though not essential, that the vehicle be composed of substances on the U.S. Food and Drug Administration (FDA) Generally Recognized as Safe (GRAS) list. Non-limiting examples include some epoxy resins, acrylates, silicone, other polymerizing materials, rubbers, and proteins including keratin, collagen, and casein. Further, it may be desirable to avoid formulations that contain common allergens (e.g. latex), emit toxic irritants as a byproduct of polymerization (e.g. aldehydes), decompose, are readily digested by dermatophytes, contain carcinogens that can be released into viable tissues around the nail, or that can cause injury by heat released during polymerization. However, if a chosen polymerization reaction releases non-toxic small molecules, the rate of release should be low enough that injury is avoided. For example, silicone rubber preparations may release acetic acid during polymerization. Acetic acid is non-toxic, but it can be irritating with prolonged application at high concentration. Therefore, if additional acetic acid has been added to the vehicle as a volatile inhibitor of polymerization, the treatment may become irritating. Therefore, steps should be taken to ensure a rate of release of non-toxic small molecules remains low enough to avoid irritation. Additionally or alternatively, it may be preferred to use alternative activators in order to avoid the release of byproducts. For example, silicone rubber preparations may be activated without releasing byproducts by using a platinum activator.

Another important feature of the vehicle according to the present disclosure is its ability to flow into deep narrow channels created by laser ablation of the infected nail. This ability requires sufficiently low viscosity and low surface tension between the vehicle and the nail. Therefore, it may be desirable, though not essential, that the vehicle change its properties after application. For example, the vehicle may begin as a flowable material and then transition to a solid material after application. More specifically, the vehicle may flow or be readily forced into laser ablated channels 140 as a liquid, and thereafter may be substantially stable for a duration of time without loosening from the channels 140 by transitioning to a solid.

Figure 14:
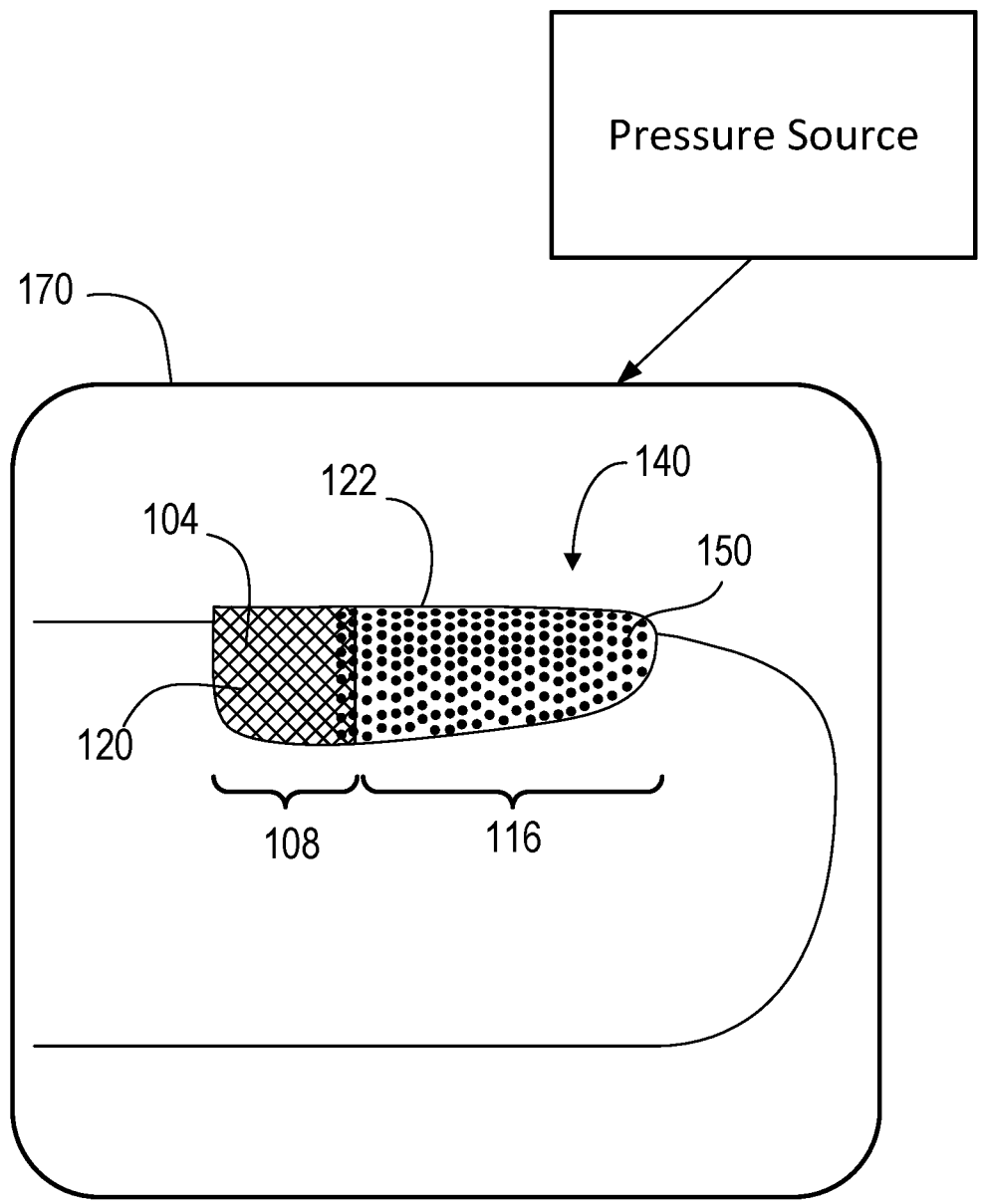
FIG. 14 is a schematic illustration of a treated nail enclosed and connected to a pressure source.

After laser processing, air fills the channels; therefore, in order for the treatment agent to flow into these small channels, trapped air and other gas within the spaces must be displaced. One approach that may be used to ensure the channels are completely filled with the treatment agent 150 is alternating air pressure at the surface of the nail. For example, as illustrated in FIG. 14, the nail 102 with the treatment agent 150 applied thereto may be at least partially enclosed and connected to a pressure source 160 that is configured to supply alternating positive and negative pressure to the nail 102. When the treatment agent 150 is placed over the channels as a liquid or gel formulation, oscillating positive and negative pneumatic pressure may cause air within the channels to expand, escape, and ultimately pump the treatment agent deeply into the channels. Due to low surface tension and flowability of the vehicle, the treatment agent 150 may progressively enter and coat the channels 140, displacing the gasses until the blind spaces are substantially full of the treatment agent 150. Additionally, a disposable chamber 170 may be used to confine the treatment agent 150 and pneumatic pressure to the nail 102 and corresponding phalanges or extremity during methods of distributing the treatment agent 150. Additionally or alternatively, other means may also be used, such as injecting the treatment agent 150 into each channel via an ablatable rigid mask.

Changing from flowable material to a material that is solid, adhesive, and strong should occur after the treatment agent 150 has flowed deeply into the channels 140 and spread under the nail plate. Therefore, timing of the change from flowable to solid may be an important feature. Timing of the change from flowable to solid may be set to a convenient time by utilizing common one-step glues, adhesives, polymers, elastomers, paints, plastics, acrylics, cyanoacrylates, etc. For example, if it takes two minutes to apply and fill the channels 140 and subungual space 118 with the treatment agent 150, and apply the optional covering layer of treatment agent 150, then the time for transition from liquid to solid should be two minutes or longer. However, this duration of time should not be so long as to be inconvenient. For example, a duration of twenty minutes or longer may be undesirable. Epoxy resins and activators may be used to facilitate a phase change in applications utilizing composite materials. After mixing a resin and activator, the material remains a flowable liquid for a predictable period of time, which can be adjusted based on its rate of polymerization. As another non-limiting example, dental resins and other flowable/formable materials used to fill, coat, bond to teeth may be implemented to facilitate a phase change in the treatment agent 150. These materials may harden spontaneously after application (e.g., as with epoxy mixtures or cyanoacrylates activated by contact with water).

Additionally or alternatively, light exposure may be employed to activate hardening of the vehicle, which may provide more control to the treatment process. Photoactivation may include creating free radicals during light exposure, which initiate chain polymerization of the material. A similar approach can be used by adding a small amount of photoactivator to the treatment agent 150. Typically, UV-A or blue light is used for photoactivation. However, the penetration of UV-A through infected nails is poor because chromophores that absorb light, such as fungal melanins, cytochromes, and others not present in normal nails, are present in the infected nail, and due to optical scattering from voids and gasses in the infected nail. Photoactivation may be preferable using wavelengths longer than 380 nm (e.g., using photoactivators that work in the 380-700 nm wavelength range). Non-limiting examples of a photoactivator may include riboflavin, rose Bengal, phthalocyanine dyes, rhodamine dyes, etc. The photoactivator may be covalently bound to one or more components of the treatment agent 150, or may be added as an independent component. Alternatively or additionally, the activator and treatment agent 150 may be delivered in separate steps of application to the nail.

In addition to the aforementioned characteristics of the treatment agent 150, the treatment agent 150 according to the present disclosure should remain chemically stable when the drug and the vehicle are combined. More specifically, the antifungal drug should be chemically stable in the environment of the laser-processed nail and the vehicle for at least as long as a treatment duration, and ideally at least as long as the infected nail takes to grow naturally and be removed by normal clipping. Further, as previously described, it may be desirable for the treatment agent 150 to change properties either naturally or as a result of light. Therefore, the drug and vehicle should remain chemically stable while changing properties and/or curing.

Additionally, another important characteristic of the treatment agent 150 is its refractive index. The refractive index of a material is a number that describes how fast light propagates through the material. Thus, the refractive index of the material largely influences the material's appearance. Therefore, it may be desirable for the treatment agent 150 to have a refractive index that closely matches a refractive index of the infected nail. Normal nails have a refractive index of approximately 1.5, and may vary between approximately 1.45-1.55 depending on the nail's hydration. Therefore, the treatment agent 150 used in the laser-assisted topical treatment according to the present disclosure may define a refractive index between 1.45 and 1.55. To achieve a refractive index within the target refractive index range, a vehicle with a refractive index between 1.45 and 1.55 may be used. Additionally or alternatively, a high or low refractive index solute may be added to the treatment agent 150 in order to achieve the target refractive index. Matching the refractive index of the treatment agent 150 with the refractive index of the nail will restore natural appearance of the nail.

Figure 15:
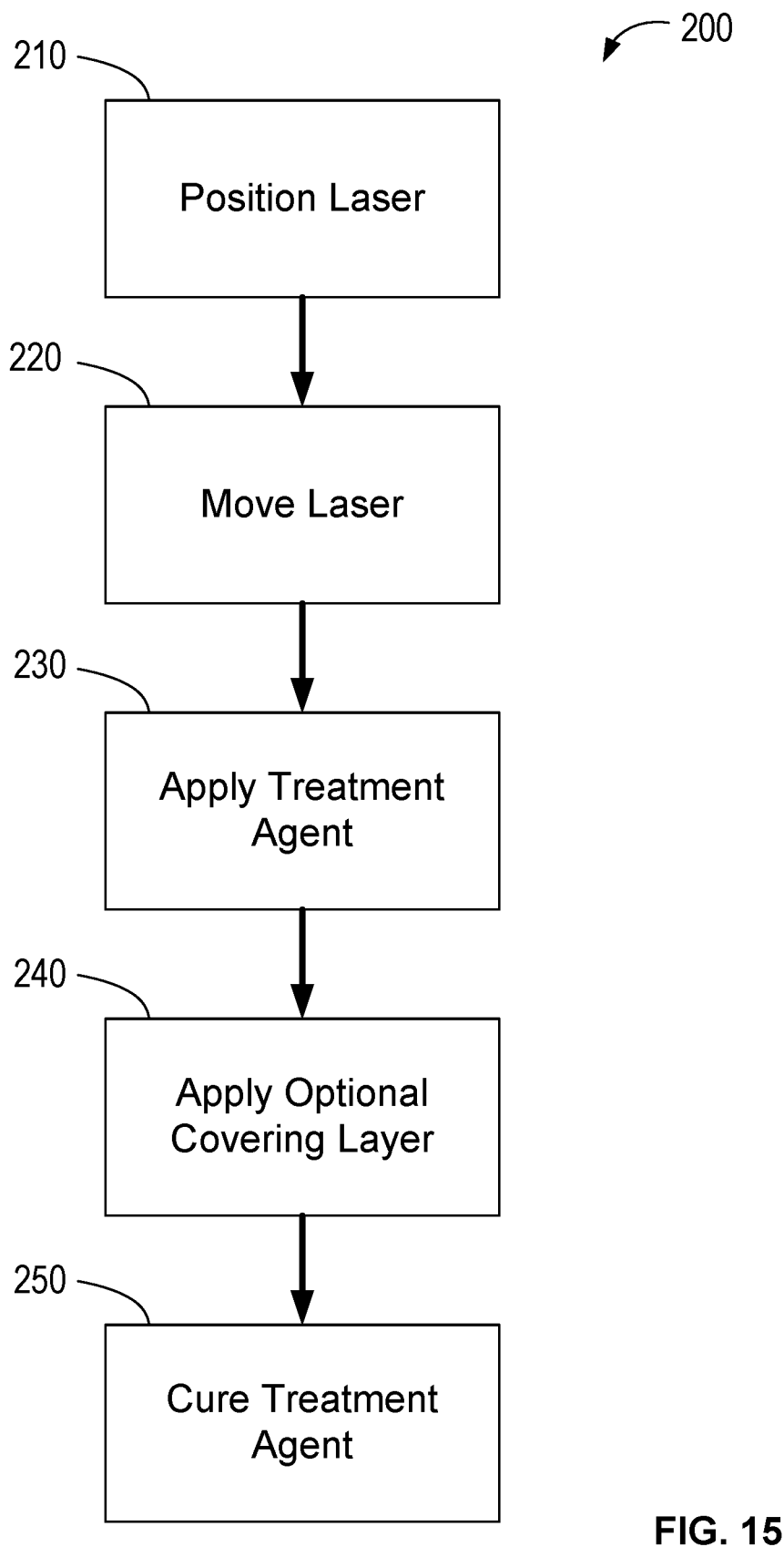
FIG. 15 is a flow chart illustrating a method for laser-assisted topical treatment according to aspects of the present disclosure.

FIG. 15 illustrates a non-limiting example of a method 200 for treating an infected nail 102 using a laser-assisted topical treatment system 10 according to the present disclosure. At step 210, a laser 20 may be positioned relative to the infected nail 102. Step 210 may further include stabilizing digits, phalanges, or extremities of the infected nail 102. The digits, phalanges, or extremities may be stabilized with straps, blocks, tape, wraps, foam, etc. Then, at step 220, the laser 20 may penetrate the surface of the infected nail 102 to create at least one channel 140 therethrough. For example, the laser may 20 create a plurality of channels 140 through the infected nail 102. Step 220 may further include moving the laser 20 along a path 130 and/or pulsing the laser 20 to create the plurality of channels 140 through the infected nail 102. Upon creating the at least one channel 140, a treatment agent 150 may be applied to an exterior surface of the infected nail 102 at step 230, The treatment agent 150 flows into the at least one channel 140. The treatment agent 150 may comprise a vehicle and a drug intended to treat onychomycosis. In order to encourage the treatment agent 150 to flow into the channels 140 completely at step 230, the method 200 may further comprise alternating positive and negative pneumatic pressure to promote distribution of the treatment agent 150 in the channels 140. For example, step 230 may further include using a disposable chamber 170 to confine the treatment agent 150 and pressure to the nail 102 and corresponding phalanges or extremity during methods of distributing the treatment agent 150. Additionally, an optional covering layer comprising at least one of the treatment agent 150, an acrylic based gel or medium, a powder based polish, or a nail lacquer may be applied to the exterior surface of the infected nail 102 at step 240, which may increase effectiveness of the treatment. Depending on the contents of the treatment agent 150, the method 200 may further require a light or heat to cure the treatment agent 150, which would be applied at step 250. Additionally or alternatively, the treatment agent may cure naturally.

Within this specification aspects have been described in a way which enables a clear and concise specification to be written, but it is intended and will be appreciated that aspects of the present disclosure may be variously combined or separated without parting from the invention. For example, it will be appreciated that all preferred features described herein are applicable to all aspects of the invention described herein.

Thus, while the invention has been described in connection with particular aspects and non-limiting examples, the invention is not necessarily so limited, and that numerous other examples, uses, modifications and departures from the examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

We claim:

1. A method for treating an infected nail using a laser, the method comprising:
   positioning the laser relative to the infected nail;
   penetrating a surface of the infected nail with a beam output by the laser to create a plurality of channels therethrough;
   applying a treatment agent to an exterior surface of the infected nail, wherein the treatment agent flows into the plurality of channels;
   enclosing the infected nail in an enclosure; and
   applying alternating positive and negative pressure to the infected nail within the enclosure to promote distribution of the treatment agent in the plurality of channels.

2. The method of claim 1, further comprising stabilizing phalanges of the infected nail.

3. The method of claim 1, further comprising moving the laser along a path while pulsing the laser to create a plurality of channels through the infected nail.

4. The method of claim 1, wherein the treatment agent comprises a vehicle and a drug.

5. The method of claim 1, further comprising applying a covering layer comprising at least one of the treatment agent, an acrylic based gel or medium, a powder based polish, or a nail lacquer to the exterior surface of the infected nail.

6. The method of claim 1, further comprising using a light to cure the treatment agent.

7. The method of claim 1, wherein the plurality of channels define widths of 250 micrometers or less.

8. The method of claim 1, wherein the plurality of channels are spaced less than 1 millimeter apart.

9. The method of claim 1, wherein the plurality of channels are spaced 50 to 200 micrometers apart.

10. The method of claim 1, wherein the treatment agent defines a refractive index between 1.45 and 1.55.

11. The method of claim 1, wherein the treatment agent include a drug that comprises terbinafine.

12. The method of claim 11, wherein the treatment agent further includes a vehicle into which the drug is embedded, and wherein the vehicle comprises a polar polymer.

13. A method for treating an infected nail using a laser, the method comprising:
   positioning the laser relative to the infected nail;
   penetrating a surface of the infected nail with a beam output by the laser to create a plurality of channels therethrough;
   applying a treatment agent to an exterior surface of the infected nail, wherein the treatment agent flows into the plurality of channels, and wherein the treatment agent defines a refractive index between 1.45 and 1.55;
   enclosing the infected nail; and
   applying alternating positive and negative pressure to the infected nail to promote distribution of the treatment agent in the plurality of channels.

14. The method of claim 13, wherein the treatment agent include a drug that comprises terbinafine.

15. The method of claim 14, wherein the treatment agent further includes a vehicle into which the drug is embedded, and wherein the vehicle comprises a polar polymer.

* * * * *